(12) United States Patent
Senthilkumar et al.

(10) Patent No.: US 7,741,478 B2
(45) Date of Patent: Jun. 22, 2010

(54) SALTS IN THE PREPARATION OF CEPHALOSPORIN ANTIBIOTICS

(75) Inventors: Udayampalayam Palanisamy Senthilkumar, Chennai (IN); Venu Sanjeevi Lakshmipathi, Chennai (IN); Gnanaprakasam Andrew, Chennai (IN); Ramasubbu Chandrasekaran, Chennai (IN); Dindigala Nagender Rao, Chennai (IN); Gaddam Om Reddy, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 217 days.

(21) Appl. No.: 11/631,595

(22) PCT Filed: Jul. 4, 2005

(86) PCT No.: PCT/IB2005/001888
§ 371 (c)(1),
(2), (4) Date: Apr. 10, 2008

(87) PCT Pub. No.: WO2006/006040
PCT Pub. Date: Jan. 19, 2006

(65) Prior Publication Data
US 2008/0306256 A1    Dec. 11, 2008

(30) Foreign Application Priority Data
Jul. 5, 2004    (IN)    ............... 637/CHE/2004

(51) Int. Cl.
*C07D 501/36* (2006.01)
*C07D 501/22* (2006.01)
*C07D 501/56* (2006.01)

(52) U.S. Cl. ............... 540/222; 540/215; 540/221; 540/227; 540/229

(58) Field of Classification Search ............... None
See application file for complete search history.

(56) References Cited

U.S. PATENT DOCUMENTS

| 3,129,224 | A |   | 4/1964 | Collins |   |
| 5,026,843 | A |   | 6/1991 | Riccardo et al. |   |
| 5,705,496 | A |   | 1/1998 | Polansky |   |
| 6,001,880 | A | * | 12/1999 | Nishino et al. | 514/617 |
| 6,350,869 | B1 |   | 2/2002 | Sturm et al. |   |
| 2005/0215781 | A1 | * | 9/2005 | Chandrasekaran et al. | 540/222 |
| 2006/0094703 | A1 | * | 5/2006 | Deshpande et al. | 540/222 |
| 2007/0244315 | A1 | * | 10/2007 | Kansal et al. | 540/219 |
| 2009/0036672 | A1 | * | 2/2009 | Pozzi et al. | 540/222 |

FOREIGN PATENT DOCUMENTS

| IN | 2003MA00456 | * | 3/2005 |
| WO | WO 2005/090360 A1 |   | 9/2005 |

\* cited by examiner

*Primary Examiner*—Mark L Berch
(74) *Attorney, Agent, or Firm*—Oliff & Berridge, PLC

(57) ABSTRACT

Compounds of general formula (II),

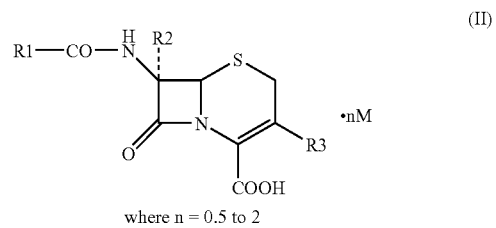

where n = 0.5 to 2 wherein $R^1$ represents

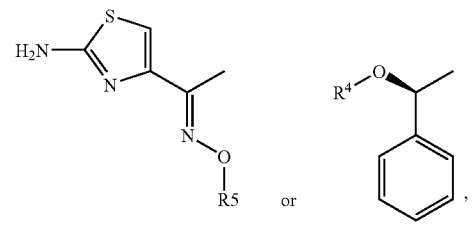

$R^4$ represents hydrogen or —CHO group, $R^5$ represents hydrogen or trityl,
$R^2$ represents hydrogen or methoxy group,
$R^3$ represents —CH=$CH_2$ or

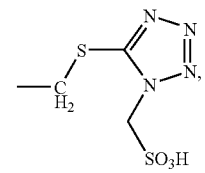

and M represents a dialkyl or dicycloalkyl ethylenediamine group selected from N,N'-diisobutylethylenediamine, N,N'-dicyclohexylethylenediamine, and N,N'-dicyclopentylethylenediamine, are useful in a process to make cephalosporin antibiotics of formula (I)

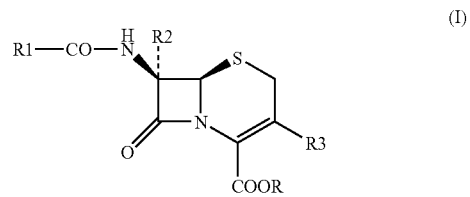

wherein R represents hydrogen or pharmaceutically acceptable esters or alkali metals salts.

9 Claims, No Drawings

SALTS IN THE PREPARATION OF CEPHALOSPORIN ANTIBIOTICS

FIELD OF THE INVENTION

The present invention relates to an improved process for the preparation of cephalosporin antibiotics of formula (I)

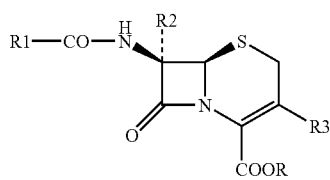
(I)

wherein R represents hydrogen or pharmaceutically acceptable alkali metal salts, or pharmaceutically acceptable esters, $R_1$ represents

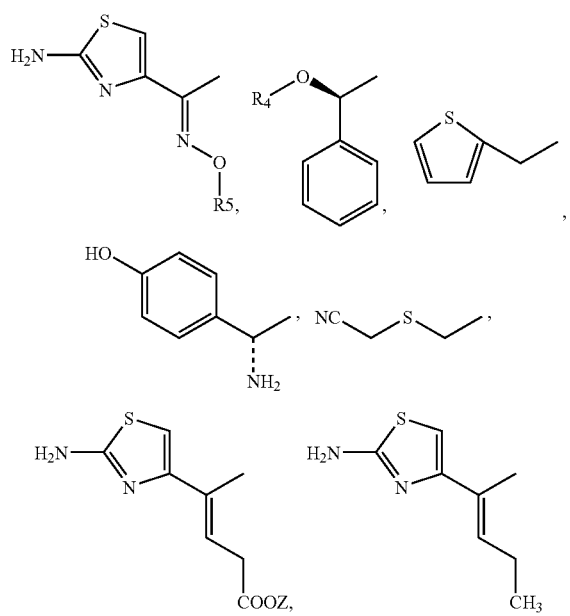

$R_4$ represents hydrogen or —CHO group; $R_5$ represents hydrogen, trityl, $CH_3$, $CR_aR_bCOOR_c$ where $R_a$ and $R_b$ independently represent hydrogen or methyl and $R_c$ represents hydrogen or ($C_1$-$C_6$)alkyl; Z represents hydrogen, $C_{1-6}$ alkyl, and substituted or unsubstituted aryl; $R_2$ represents hydrogen or methoxy group; $R_3$ represents hydrogen, —$CH_3$, —$CH_2OCOCH_3$, —$CH$=$CH_2$, —$CH_2$—O—CO—$NH_2$, —$CH$=$CH$—$CH_3$ or a group represented by

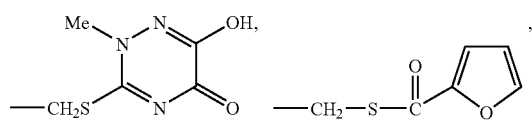

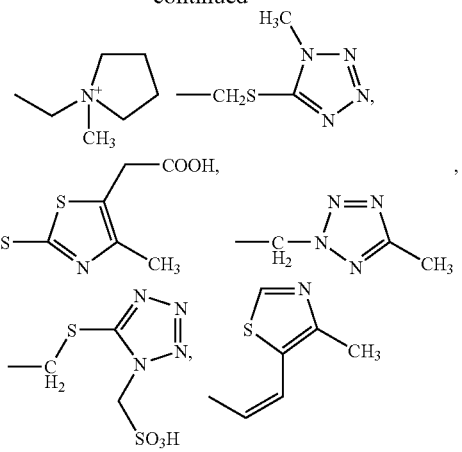

The present invention also provides new salts of compound of formula (II)

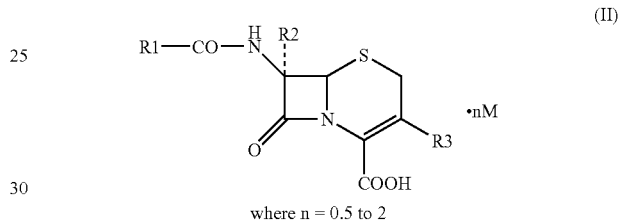
(II)

where n = 0.5 to 2 wherein $R_1$, $R_2$ and $R_3$ are defined as above and M represents the compound of formula (III)

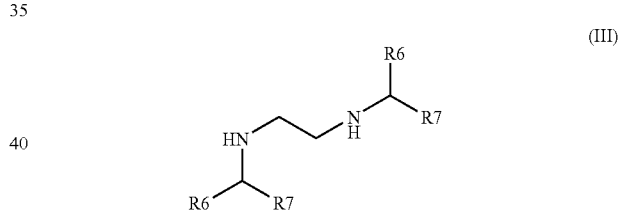
(III)

wherein $R_6$, $R_7$ may be identical or different and are each, independently of one another, represent a linear or branched alkyl having from 1 to 8 carbon atoms or together with the C atom to which they are bound form a 3- to 8-membered saturated ring which may be further substituted or substituted aryl ring;

The present invention also provides a process for the preparation of compound of formula (I) using the new salts of formula (II).

BACKGROUND OF THE INVENTION

U.S. Pat. No. 6,350,869 discloses the purification of impure cefdinir through the preparation of N,N-dicyclohexylamine salt of 7-[2-aminothiazol-4-yl-2-(z)-hydroxyimino acetamido]-3-vinyl-3-cephem-4-carboxylic acid and subsequent hydrolysis to get pure cefdinir. This process requires the preparation of crude cefdinir, conversion to N,N-dicyclohexylamine salt and then hydrolysis of the salt to get pure cefdinir, and therefore the overall yield is not attractive.

U.S. Pat. No. 5,705,496 discloses a process for preparing the benzathine salt of Cefonicid which comprises treating an aqueous solution or suspension of Cefonicid with an organic solvent and N,N'-dibenzylethylenediamine.

U.S. Pat. No. 5,026,843 discloses the process for the preparation of Ceftriaxone disodium hemiheptahydrate involving condensing 7-ACT with MAEM. The product formed is precipitated by using dibenzylethylenediamine and subsequently is treated with sodium ethylhexanoate in acetone.

In order to get rid of impurities and isolating the product from aqueous medium, all these prior art references used different kind of amine salt with cephem-4-carboxylic acid derivatives. But none of the processes gave desired yield and quantity.

In continuation of our research, for developing new and efficient processes for making cephlosporins, we have found new salts of formula (II) and its use in the preparation of cephalosporin antibiotics of the formula (I) with minimum impurities in high yield.

OBJECTIVES OF THE INVENTION

The main objective of the present invention is to provide new salts of compound of formula (II), which are stable throughout the process for the preparation of cephalosporin antibiotics of the formula (I).

Another objective of the present invention is to provide a process for the preparation of cephalosporin antibiotics of formula (I) using these new salts.

Another objective of the present invention is to prepare cephalosporin antibiotics of formula (I) that are highly pure, high yielding and cost effective, which would be easy to implement on manufacturing scale.

Still another objective of the present invention is to provide a process for the preparation of new salts of formula (II).

SUMMARY OF THE INVENTION

Accordingly, the present invention provides new salts of the compound of formula (II),

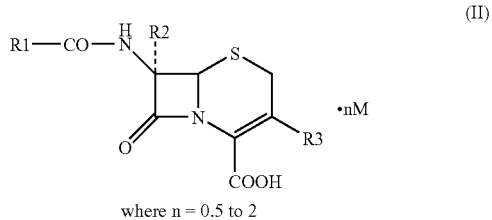

where n = 0.5 to 2 wherein $R_1$, $R_2$, $R_3$ are as defined above; and M represents the compound of formula (III),

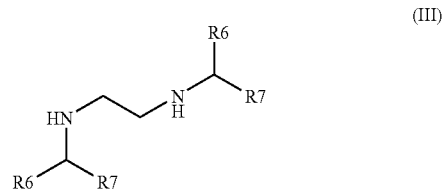

wherein $R_6$, $R_7$ may be identical or different and are each, independently of one another, represent a linear or branched alkyl having from 1 to 8 carbon atoms or together with the C atom to which they are bound form a 3- to 8-membered saturated ring which may be further substituted or substituted aryl ring;

Another embodiment of the present invention is to provide a process for the preparation of compound of the formula (I), which comprises i) condensing the compound of the formula (IV) or its salts or its trimethylsilyl esters with compound of formula (V) wherein Y is a group which forms a basis that a compound of formula (V) is in a reactive form; including halogen, a group which forms together with the —C=O group to which Y is attached an active ester, thioester, and a group which forms together with the —C=O group to which Y is attached a mixed anhydride in the presence or absence of a base and solvent to produce compound of formula (VI), ii) treating the compound of formula (VI) with compound of formula (III) to produce the compound of formula (II), and iii) treating the compound of formula (II) either with an acid or with sodium exchanging reagent to produce the compound of formula (I).

The process is shown in the Scheme-I

Scheme-I

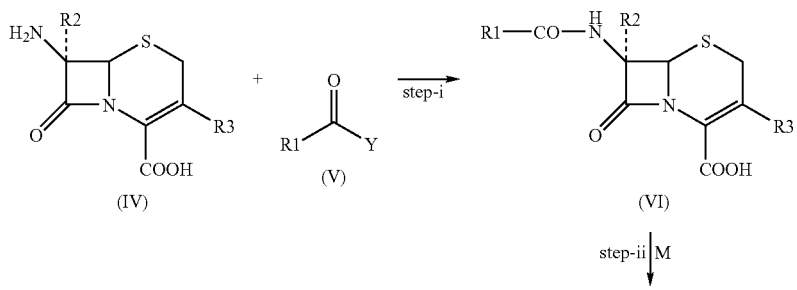

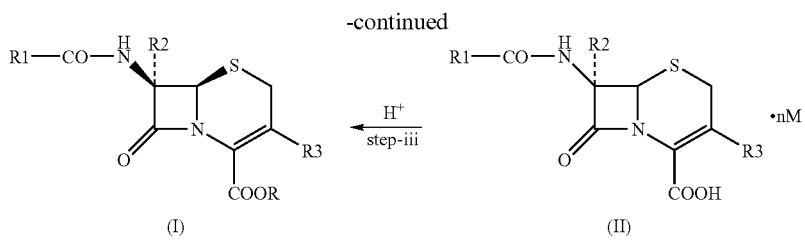

-continued

DETAILED DESCRIPTION OF THE INVENTION

In an embodiment of the present invention, the base used in step (i) is selected from sodium hydroxide, sodium acetate, potassium hydroxide, ammonium hydroxide, sodium carbonate, potassium carbonate, sodium bicarbonate triethylamine, trimethylamine, N-methylpiperidine, diethylamine, tributylamine, pyridine, N-alkylanilines, N,N-diisopropylethylamine N-methylmorpholine, and the like or mixtures thereof.

In another embodiment of the present invention the reaction in step (i) is carried out at a temperature ranging from −50° C. to +80° C.

In an another embodiment of the present invention, the solvent used in step (i) is selected from ethanol, methanol, isopropanol, THF, cyclohexanol, acetonitrile, DMAc, DMF, N-methylpyrrolidine, ethyl acetate, methylene dichloride, ethylene dichloride, acetone, toluene, tetrahydrofuran, xylene, water or mixtures thereof.

In yet another embodiment of the present invention, Y is a group which forms a basis that a compound of formula (V) is in a reactive form; including chlorine, bromine, fluorine and iodine, a group which forms together with the —C=O group to which Y is attached an active ester, thioester, and a group which forms together with the —C=O group to which Y is attached a mixed anhydride. Illustrative example of those active esters includes benzothiazole, benzoxazole, benzotriazole or benzimidazole.

In yet another embodiment of the present invention, M is selected from N,N'-Diisobutylethylenediamine, N,N'-Dicyclohexylethylenediamine or N,N'-Di-(p-anisyl)1ethylenediamine, N,N'-Dicyclopentylethylenediamine and N,N'-(p-tolyl)1ethylenediamine In yet another embodiment of the present invention, the solvent used in step (ii) is selected from ethanol, methanol, isopropanol, acetonitrile, acetone, ethylacetate, THF, DMAc, DMF, water or mixtures thereof.

In still another embodiment of the present invention the acid employed in step (iii) is selected from HCl, sulfuric acid, formic acid, acetic acid, perchloric acid, benzenesulfonic acid, p-toluenesulfonic acid, naphthalenesulfonic acid, methanesulfonic acid, trifluoro acetic acid, DIAION® UBK530 resin, (a cationic exchange resin of general formula),

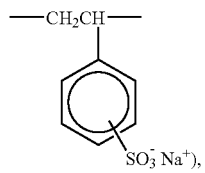

cationic exchange resin or mixtures thereof.

In still another embodiment of the present invention, wherein the sodium exchanging reagent is selected from sodium acetate, sodium citrate, sodium lactate, sodium ethylacetoacetate and sodium 2-ethylhexanoate and the solvent used for dissolving the reagent is selected from ethanol, methanol, isopropanol, acetonitrile, ethyl acetate, acetone, water or mixtures thereof.

In another embodiment of the present invention the novel salts prepared in accordance with this invention is useful in the isolation of cephalosporin antibiotics such as Cefonicid, Cefdinir, Cefoxitin, Cefditoren, Cefixime, Cefepime in pure and good yield.

In one more embodiment of the present invention the starting material of formula (IV) is prepared by utilizing the scheme available in the prior art.

The present invention is illustrated with the following examples, which should not be construed as limiting to the scope of the invention.

EXAMPLE 1

Step-(i)

N,N'-Diisobutylethylenediamine salt of 7-D-mandelamido-3-(((1-sulfomethyl-1H-tetrazol-5-yl)thio) methyl)-3-cephem-4-carboxylic acid 7-amino-3-(1-sulfomethyl-1H-tetrazol-5-yl)thiomethyl-3-cephem-4-carboxylic acid (5 g) was dissolved in water (19 ml) using 30% w/w sodium hydroxide (1.5 g in 8 ml water) and sodium bicarbonate (1 g), O-formylmandeloyl chloride (2.45 g) was added at 0-5° C. and maintained at 5-10° C. over a period of 1-2 hours. After the completion of reaction, the reaction mixture was acidified with conc. HCl (2.6 g) and maintained the reaction at 28-30° C. for about 2-3 hrs, sodium bicarbonate (3.5 g) was added to set the pH 5±1 and the reaction mass solution was added to a solution of N,N'-diisobutylethylenediamine diacetate (8.2 g) in water (40 mL) and isopropyl alcohol (40 mL) and stirred well at 25-30° C. for about 2-3 hours. The reaction mixture was cooled to 5-10° C., filtered, washed with chilled water (0-5° C.) followed by isopropyl alcohol (0-5° C.) and dried the material at ~40° C. to get N,N'-diisobutylethylenediamine salt of 7-D-mandelamido-3-(((1-sulfomethyl-1H-tetrazol-5-yl)thio)methyl)-3-cephem-4-carboxylic acid (5.5 g).

Step(ii)

7-D-Mandelamido-3-(((1-sulfomethyl-1H-tetrazol-5-yl)thio)methyl)-3-cephem-4-carboxylic acid, sodium salt N,N'-diisobutylethylenediamine salt of 7-D-mandelamido-3-(((1-sulfomethyl-1H-tetrazol-5-yl)thio)methyl)-3-cephem-4-carboxylic acid (2.0 g) was charged into a mixture of isopropyl alcohol (20 mL) and acetone (4 mL) followed by DIAION® UBK530 resin (5 g) and stirred the reaction mixture for 2-4 hours at 25-30° C. The reaction mixture was filtered and washed the resin using acetone (10 mL). To the clear filtrate, a solution of sodium 2-ethylhexanoate (1.0 g in 5 ml acetone) was added at 25-30° C., stirred for 1 hour, filtered, washed with acetone, and dried the material under vacuum to yield 7-D-mandelamido-3-(((1-sulfomethyl-1H-tetrazol-5-yl)thio)methyl)-3-cephem-4-carboxylic acid, sodium salt (1.4 g).

EXAMPLE 2

Step-(i)

N,N'-Dicyclohexylethylenediamine salt of 7-D-mandelamido-3-(((1-sulfomethyl-1H-tetrazol-5-yl)thio) methyl)-3-cephem-4-carboxylic acid 7-amino-3-(sulfomethyl-1H-tetrazol-5-yl)thiomethyl-3-cephem-4-carboxylic acid (5 g), was dissolved in water (19 ml) using 30% w/w sodium hydroxide (1.5 g in 8 ml water) and sodium bicarbonate (1 g), O-formylmandeloyl chloride (2.45 g) was added at 0-5° C. and maintained at 5-10° C. over a period of 1-2 hours. After the completion of reaction, the reaction mixture was acidified with conc. HCl (2.6 g) and maintained the reaction at 28-30° C. for about 2-3 hours. After the completion of reaction, sodium bicarbonate (~3.5 g) was added to set the pH 5±1 and the solution was added to a solution of N,N'-dicyclohexylethylenediamine diacetate (9.26 g) in water (40 mL) and isopropyl alcohol (40 mL) and stirred well at 25-30° C. for about 2-3 hours. The reaction mixture was cooled to 5-10° C., filtered, washed with chilled water (0-5° C.) and isopropyl alcohol (0-5° C.) and dried the material under vacuum at ~40° C. to get N,N'-dicyclohexylethylenediamine salt of 7-D-mandelamido-3-(1-sulfomethyl-1H-tetrazol-5-yl)thio)methyl)-3-cephem-4-carboxylic acid (6.5 g).

Step-(ii)

7-D-Mandelamido-3-(((1-sulfomethyl-1H-tetrazol-5-yl)thio)methyl)-3-cephem-4-carboxylic acid, sodium salt N,N'-dicyclohexylethylenediamine salt of 7-D-mandelamido-3-(((1-sulfomethyl-1H-tetrazol-5-yl)thio)methyl)-3-cephem-4-carboxylic acid (2.0 g) was charged into a mixture of isopropyl alcohol (20 mL) and acetone (4 mL) followed by DIAION® UBK530 resin (5 g) at 25-30° C. and stirred for 2-4 hours, filtered the reaction mass and washed the resin with acetone (10 mL). To the filtrate, a solution of sodium 2-ethylhexanoate (0.97 g in 5 ml acetone) was added at 25-30° C. and stirred for about 1 hour, filtered, washed with acetone, and dried the material under vacuum to yield 7-D-mandelamido-3-(((1-sulfomethyl 1H-tetrazol-5-yl)thio)methyl)-3-cephem-4-carboxylic acid, sodium salt (1.4 g).

EXAMPLE 3

Step(i)

N,N'-Di-(p-anisyl)ethylenediamine salt of 7-D-mandelamido-3-(((1-sulfomethyl-1H-tetrazol-5-yl)thio) methyl)-3-cephem-4-carboxylic acid 7-amino-3-(1-sulfomethyl-1H-tetrazol-5-yl)thiomethyl-3-cephem-4-carboxylic acid (5 g) was dissolved in water (19 ml) using 30% w/w sodium hydroxide (1.5 g in 8 ml water) and sodium bicarbonate (1 g), O-formylmandeloyl chloride (2.45 g) was added at 0-5° C. and maintained at 5-10° C. over a period of 1-2 hours. After the completion of reaction, the reaction mixture was acidified with conc. HCl (2.6 g) and maintained under stirring at 28-30° C. over 2-3 hours. After the completion of reaction, sodium bicarbonate (~3.5 g) was added to set the pH 5±1. The solution was added to a solution of N,N'-di-(p-anisyl)ethylenediamine diacetate (11.7 g) in water (40 mL) and isopropyl alcohol (40 mL) and stirred well at 25-30° C. After stirring for 2-3 hours, the reaction mixture was cooled to 5-10° C., filtered, washed with chilled water (0-5° C.) and isopropyl alcohol (0-5° C.) and dried the material under vacuum at ~40° C. to get N,N'-di-(p-anisyl)ethylenediamine salt of 7-D-mandelamido-3-(((1-sulfomethyl-1H-tetrazol-5-yl)thio)methyl)-3-cephem-4-carboxylic acid (6.4 g).

Step-(ii)

7-D-Mandelamido-3-(((1-sulfomethyl-1H-tetrazol-5-yl)thio)methyl)-3-cephem-4-carboxylic acid, sodium salt N,N'-di-(p-anisyl)ethylenediamine salt of 7-D-mandelamido-3-(((1-sulfomethyl-1H-tetrazol-5-yl)thio)methyl)-3-cephem-4-carboxylic acid (2.0 g) was charged into a mixture of isopropyl alcohol (20 mL) and acetone (4 mL) followed by DIAION® UBK530 resin (5 g) at 25-30° C. and stirred for 2-4 hours. The reaction mixture was filtered, washed with acetone (10 mL). To the filtrate, a solution of sodium 2-ethylhexanoate (0.86 g in 5 ml acetone) was added at 25-30° C., stirred for 1 hour, filtered, washed with acetone, and dried the material under vacuum to yield 7-D-mandelamido-3-(((1-sulfomethyl-1H-tetrazol-5-yl) thio)methyl)-3-cephem-4-carboxylic acid, sodium salt (1.5 g).

EXAMPLE: 4

Step-i

Preparation of N,N'-dicyclohexylethane-1,2-diammonium 7β-[2-(2-amino-4-thiazolyl)-2-(Z-trityloxyimino)acetamido]-3-vinyl-3-cephem-4-carboxylate 7-amino-3-vinyl-3-cephem-4-carboxylic acid (10 gm) was taken in a mixture of tetrahydrofuran (60 ml) and water (5 ml), triethylamine (9.0 gm) was added drop-wise at 20±2° C. over 30-45 minutes. 2-mercaptobenzothiazolyl (Z)-(2-aminothiazol-4-yl)-2-(trityloxyimino)acetate (26 gm) was added to the clear solution and the resulting mixture was stirred at 32±2° C. for 4-6 hours. After completion of the reaction, the reaction mixture was cooled to 20±2° C., ethyl acetate (200 ml) and water (250 ml) were added and stirred for 10 min. The pH of the reaction mixture was adjusted to 3.50-4.00 by 1:1 HCl (20.0 ml) in 30 min. The layers were separated; ethyl acetate layer was washed with 20% sodium chloride solution (20 g of NaCl in 100 ml of water) and separated. The ethyl acetate layer was added dropwise in 20 min at 32±2° C. to a solution of N,N'-dicyclohexylethane-1,2-diamine in a mixture of acetonitrile (300 ml) and methanol (50 ml) and stirred for 25 min. The resulting slurry was filtered, washed with acetonitrile (100 ml) and dried at 30-35° C. under vacuum to obtain N,N'-dicyclohexylethane-1,2-diammonium 7β-[2-(2-amino-4-thiazolyl)-2-(Z-trityloxyimino)acetamido]-3-vinyl-3-cephem-4-carboxylate (30.1 gm, HPLC Purity 93.74%)

Step-ii

Preparation of N,N'-dicyclohexylethane-1,2-diammonium 7β-[2-(2-amino-4-thiazolyl)-2-(Z-hydroxyimino)acetamido]-3-vinyl-3-cephem-4-carboxylate from N,N'-dicyclohexylethane-1,2-diammonium 7β-[2-(2-amino-4-thiazolyl)-2-(Z-trityloxyimino)acetamido]-3-vinyl-3-cephem-4-carboxylate A mixture of N,N'-dicyclohexylethane-1,2-diammonium 7β-[2-(2-amino-4-thiazolyl)-2-(Z-trityloxyimino)acetamido]-3-vinyl-3-cephem-4-carboxylate (50 gm) and 2.5 gm of activated carbon was added to a mixture of acetonitrile (150 ml) and water (21 ml) and heated to 50° C. The reaction mixture was heated to 60-62° C. in 20 minutes, hydrochloric acid (34 ml, 1:1 v/v) and maintained at this temperature for 35 minutes. At $36^{th}$ minute 300 ml of chilled 1;1 mixture of acetone and isopropanol having temperature −15° C. was added to the reaction mixture to reduce the temperature to 30-35° C. The carbon was filtered and the carbon bed was washed with acetone (100 ml). A methanolic solution of N,N'-dicyclohexylethane-1,2-diamine (10 gm in 25 ml of methanol) was added to the filtrate dropwise over 30 minutes to adjust the pH of the solution to 6.5-6.75 at 35° C. and stirred for 30 minutes. The resulting slurry was stirred for 15-20 minutes at 33-35° C., cooled to 25° C., and stirred for 30 minutes. The product thus obtained was filtered, washed with 100 ml of acetone and dried at 35° C. under vacuum for 3-4 hours to get the 40.0 gm of N,N'-dicyclohexylethane-1,2-diammonium 7β-[2-(2-amino-4-thiazolyl)-2-(Z-hydroxyimino)acetamido]-3-vinyl-3-cephem-4-carboxylate (HPLC purity<98%).

Step-iii

Preparation of 7-[[(2-aminothiazol-4-yl)-(z)(hydroxyimino)]acetyl]amino-3-vinyl-3-cephem-4-carboxylic acid from N,N'-dicyclohexylethane-1,2-diammonium 7β-[2-(2-amino-4-thiazolyl)-2-(Z-hydroxyimino)acetamido]-3-vinyl-3-cephem-4-carboxylate N,N'-dicyclohexylethane-1,2-diammonium 7β-[2-(2-amino-4-thiazolyl)-2-(Z-hydroxyimino)acetamido]-3-vinyl-3-cephem-4-carboxylate (20 gm) was added to a solution of acetone 80 ml in water 600 ml at 32-36° C., dissolved by hydrochloric acid (25 ml) at pH 1.25 to 1.75 in 5-10 minutes, and adjust the pH to 5.4-5.6 by ammonia (15 ml 15%). The aqueous solution was treated with carbon and EDTA at 30-34° C. for 30 min. Carbon was filtered, washed with water (80 ml) and the pH was adjusted to 2.5-2.6 by 20% sulphuric acid cooled to 25-27° C. After 30 minutes being stirred, the product was filtered, washed with 50 ml of cold-water, followed by acetone (25 ml) and dried in air at 28-32° C. for 3-5 hrs to get 7.95 gm of 7-[[(2-aminothiazol-4-yl)-(z)(hydroxyimino)]acetyl]amino-3-vinyl-3-cephem-4-carboxylic acid [HPLC quality >99.0%].

EXAMPLE 5

Preparation of N,N'-dicyclohexylethane-1,2-diammonium 7β-[2-(2-amino-4-thiazolyl)-2-(Z-hydroxyimino)acetamido]-3-vinyl-3-cephem-4-carboxylate from potassium 7β-[2-(2-amino-4-thiazolyl)-2-(Z-trityloxyimino)acetamido]-3-vinyl-3-cephem-4-carboxylate A mixture of 50 gm of potassium 7-[[2-(2-aminothiazol-4-yl)-(z)-2-(trityloxyimino)]acetyl]amino-3-vinyl-3-cephem-4-carboxylate and carbon (2.5 gm) was added to a mixture of acetone 55 ml and water 21 ml and heated to 50° C. The reaction mixture was heated to 60-62° C. in 20 minutes, hydrochloric acid (34 ml, 1:1 v/v) and maintained at 65-67° C. for 35 minutes. At $36^{th}$ minute, a 1:1 mixture of 400 ml of acetone and isopropanol having temperature −15° C. was added to the reaction mixture to reduce the temperature to 30-35° C. The carbon was filtered and the carbon bed was washed with acetone (100 ml). A methanolic solution of N,N'-dicyclohexylethane-1,2-diamine (10 gm in 25 ml of methanol) was added to the filtrate dropwise over 30 minutes to adjust the pH of the solution to 6.5-7.0 at 35° C. and stirred for 30 minutes. The resulting slurry was stirred for 15-20 minutes at 33-35° C., cooled to 25° C., and stirred for 30 minutes. The product thus obtained was filtered, washed with 100 ml of acetone and dried at 35° C. under vacuum for 3-4 hours to get the 36.0 gm of N,N'-dicyclohexylethane-1,2-diammonium 7β-[2-(2-amino-4-thiazolyl)-2-(Z-hydroxyimino)acetamido]-3-vinyl-3-cephem-4-carboxylate (HPLC purity<98%).

EXAMPLE: 6

Preparation of N,N'-dicyclohexylethane-1,2-diammonium 7β-[2-(2-amino-4-thiazolyl)-2-(Z-hydroxyimino)acetamido]-3-vinyl-3-cephem-4-carboxylate from dicyclohexylammonium 7β-[2-(2-amino-4-thiazolyl)-2-(Z-trityloxyimino)acetamido]-3-vinyl-3-cephem-4-carboxylate A mixture of dicyclohexylammonium 7β-[2-(2-amino-4-thiazolyl)-2-(Z-trityloxyimino)acetamido]-3-vinyl-3-cephem-4-carboxylate (50 gm) and 2.5 gm of activated carbon was added to a mixture of acetonitrile (150 ml) and water (21 ml) and heated to 50° C. The reaction mixture was heated to 60-62° C. in 20 minutes, hydrochloric acid (34 ml, 1:1 v/v) and maintained at 65-67° C. for 35 minutes. At $36^{th}$ minute, a chilled mixture of 300 ml of acetone and isopropanol having temperature −15° C. was added to the reaction mixture to reduce the temperature to 30-35° C. The carbon was filtered and the carbon bed was washed with acetone (100 ml). A methanolic solution of N,N'-dicyclohexylethane-1,2-diamine (10 gm in 25 ml of methanol) was added to the filtrate dropwise over 30 minutes to adjust the pH of the solution to 6.5-7.0 at 35° C. and stirred for 30 minutes. The resulting slurry was stirred for 15-20 minutes at 33-35° C., cooled to 25° C., and stirred for 30 minutes. The product thus obtained was filtered, washed with 100 ml of acetone and dried at 35° C. under vacuum for 3-4 hours to get the 42.0 gm of N,N'-dicyclohexylethane-1,2-diammonium 7β-[2-(2-amino-4-thiazolyl)-2-(Z-hydroxyimino)acetamido]-3-vinyl-3-cephem-4-carboxylate.

EXAMPLE 7

N,N'-Diisopentylethylenediamine salt of 7-D-mandelamido-3-(((1-sulfomethyl-1H-tetrazol-5-yl)thio)methyl)-3-cephem-4-carboxylic acid 7-amino-3-(1-sulfomethyl-1H-tetrazol-5-yl)thiomethyl-3-cephem-4-carboxylic acid (25 g) was dissolved in water (110 ml) using sodium bicarbonate (4 g) at 0-5° C. in 2.0 hrs, O-formylmandeloyl chloride (12.5 g) was added at 0-5° C. and maintained at 5-10° C. over a period of 0.5-1.0 hours. After the completion of reaction, the reaction mixture was acidified with conc. HCl (15-16 mL) and maintained the reaction at 28-30° C. for about 2-3 hrs. To the reaction mass, mixture of Methylene dichloride and Tetrahydrofuran are charged and separated the aqueous layer. Aqueous layer pH was adjusted to 4.0 using 15% ammonia solution at 28-30° C. for a period of 0.5-1.0 hour. The reaction mass solution was added to a solution of N,N'-diisopentylethylenediamine diacetate (20.2 g) in water (88 mL) in presence of Tetrahydrofuran and stirred well at 25-30° C. for about 2-3 hours. The reaction mixture was cooled to 5-10° C., filtered, washed with chilled water (0-5° C.) and dried the material at ~40° C. to get N,N'-diisopentylethylenediamine salt of 7-D-mandelamido-3-(((1-sulfomethyl-1H-tetrazol-5-yl)thio)methyl)-3-cephem-4-carboxylic acid (38 g).

EXAMPLE 8

N,N'-(p-tolyl)ethylenediamine salt of 7-D-mandelamido-3-(((1-sulfomethyl-1H-tetrazol-5-yl)thio)methyl)-3-cephem-4-carboxylic acid 7-amino-3-(1-sulfomethyl-1H-tetrazol-5-yl)thiomethyl-3-cephem-4-carboxylic acid (25 g) was dissolved in water (110 ml) using sodium bicarbonate (4 g) at 0-5° C. in 2.0 hrs, O-formylmandeloyl chloride (12.5 g) was added at 0-5° C. and maintained at 5-10° C. over a period of 0.5-1.0 hours. After the completion of reaction, the reaction mixture was acidified with conc. HCl (15-16 mL) and maintained the reaction at 28-30° C. for about 2-3 hrs. To the reaction mass, mixture of Methylene dichloride and Tetrahydrofuran are charged and separated the aqueous layer. Aqueous layer pH was adjusted to 4.0 using 15% ammonia solution at 28-30° C. for a period of 0.5-1.0 hour. The reaction mass solution was added to a solution of N,N'-(p-tolyl)ethylenediamine diacetate (23 g) in water (92 mL) in presence of Tetrahydrofuran and stirred well at 25-30° C. for about 2-3 hours. The reaction mixture was cooled to 5-10° C., filtered, washed with chilled water (0-5° C.) and dried the material at ~40° C. to get N,N'-(p-tolyl)ethylenediamine salt of 7-D-mandelamido-3-(((1-sulfomethyl-1H-tetrazol-5-yl)thio)methyl)-3-cephem-4-carboxylic acid (38 g).

EXAMPLE 9

Preparation of 7β-[2-(2-amino-4-thiazolyl)-2-(Z-hydroxyimino)acetamido]-3-vinyl-3-cephem-4-carboxylic acid (cefdinir)

Step-i Preparation of N,N'-Dicyclohexylethylenediamine salt of 7β-[2-(2-amino-4-thiazolyl)-2-(Z-hydroxyimino)acetamido]-3-vinyl-3-cephem-4-carboxylic acid (Cefdinir-DDA)

To a chilled suspension of 7-amino-3-vinyl-3-cephem-4-carboxylic acid (50 gm) in a mixture of tetrahydrofuran (250 ml) and water (31.5 ml), triethylamine (45 gm) was added dropwise at 20±2° C. over 30-45 minutes. 2-mercaptobenzothiazolyl (Z)-(2-aminothiazol-4-yl)-2-(trityloxyimino)acetate (130 gm) was added to the clear solution and the resulting mixture was stirred at 32±2° C. for 4-6 hours. The reaction was monitored by HPLC. After the completion of reaction, THF was completely removed under vacuum at 28-30° C. To the concentrated mass, acetone (300 mL) was added and stirred at 30° C., 1:1 Hydrochloric acid (200 mL) was added and the temperature was raised to 63-64° C. At this temperature, it was refluxed for about 35 min and then cold acetone of 1.8 Liter dumped to the reaction mass to bring down the temperature to 30° C., EDTA (0.5 g) was added and stirred for 10 min at 30-35° C., pH of the solution was adjusted to 2.5 using Triethyl amine (100 mL) at 30-35° C. To the reaction mixture hot solution of N,N'-Dicyclohexylethylenediamine (DDA) 40.0 g in Isopropyl alcohol (100 mL) was added slowly to adjust the pH of the solution 5.5 and stirred for 1.0 hour at 30-35° C.

The precipitated material was filtered, washed with acetone and dried under vacuum at ~40° C. to get N,N'-Dicyclohexylethylenediamine salt of 7β-[2-(2-amino-4-thiazolyl)-2-(Z-hydroxyimino)acetamido]-3-vinyl-3-cephem-4-carboxylic acid.

Step-ii

Preparation of Cefdinir from Cefdinir-DDA

Cefdinir-DDA (100 g) was stirred in a mixture of acetone (200 mL) and water (3.0 Lt) at 35-38° C., pH of the solution was adjusted to 1.5 using 1:1 HCl in 5-10 minutes then pH of the solution was readjusted to 6.0 using aqueous ammonia solution (70 mL) at 35-38° C. To the resulting solution, carbon (10 g) was added stirred for 20-25 minutes and filtered. pH of the clear filtrate was adjusted to 2.5 with 1:1 hydrochloric acid (50 mL) to precipitate Cefdinir. The precipitate was stirred for 3.0 hrs at 30-35° C., filtered and washed the wet cake with water (500 mL). Wet material is dried under vacuum to get 46.0 g of Cefdinir.

We claim:
1. A compound of general formula (II)

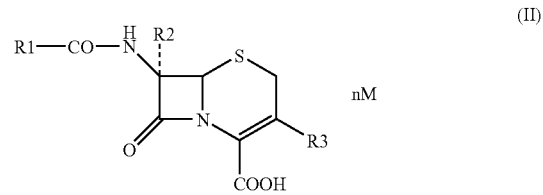

where n = 0.5 to 2 wherein $R^1$ represents

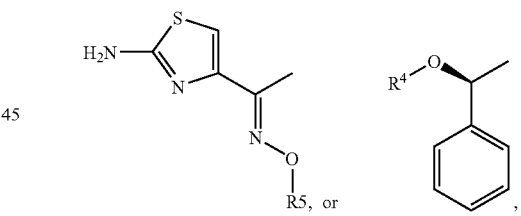

$R^4$ represents hydrogen or —CHO group, $R^5$ represents hydrogen or trityl, $R^2$ represents hydrogen or methoxy group, $R^3$ represents —CH=CH$_2$ or

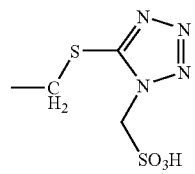

wherein M represents a dialkyl or dicycloalkyl ethylenediamine group selected from N,N'-diisobutylethylenediamine, N,N'-dicyclohexylethylenediamine, and N,N'-dicyclopentylethylenediamine.

2. A compound of formula

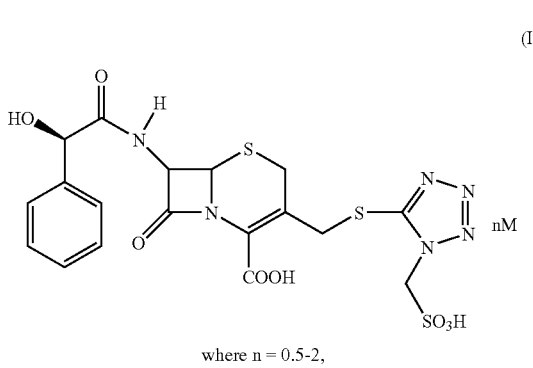

(III)

where n = 0.5-2, wherein M represents N,N'-diisobutylethylenediamine, N,N'-dicyclohexylethylenediamine, or N,N'-dicyclopentylethylenediamine.

3. A compound of formula

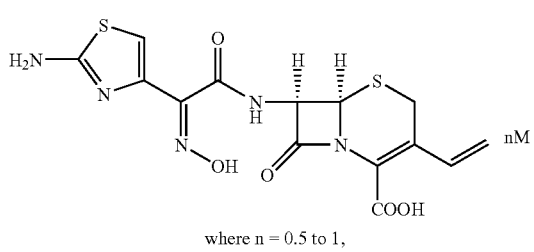

(IV)

where n = 0.5 to 1, wherein M represents N,N'-diisobutylethylenediamine, N,N'-dicyclohexylethylenediamine, or N,N'-dicyclopentylethylenediamine.

4. A process for the preparation of compound of formula (II),

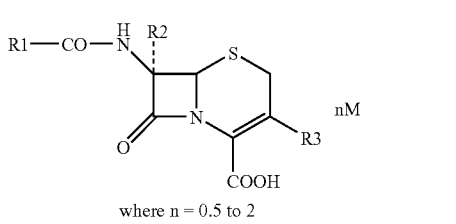

(II)

where n = 0.5 to 2 wherein $R^1$ represents

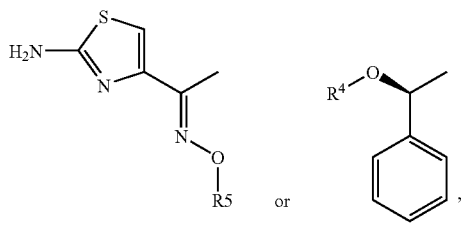

wherein $R^4$ represents hydrogen or —CHO group and $R^5$ represents hydrogen or trityl, $R^2$ represents hydrogen or methoxy group,
$R^3$ represents —CH=CH$_2$ or

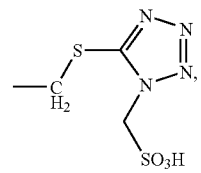

and

M represents a dialkyl or dicycloalkyl ethylenediamine group selected from N,N'-diisobutylethylenediamine, N,N'-dicyclohexylethylenediamine, and N,N'-dicyclopentylethylenediamine, the process comprising:
i) condensing a compound of formula (VI)

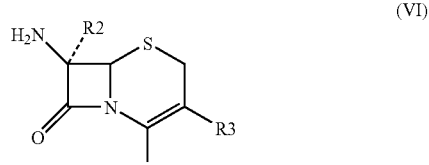

(VI)

(VII)

with a compound of formula (VII) wherein Y is selected from halogens, or a group which forms together with the —C=O group to which Y is attached an active ester, and a group which forms together with the —C=O group to which Y is attached a mixed anhydride in the presence of a base and solvent to produce a compound of formula (VIII); and

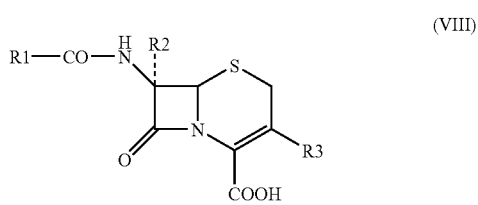

(VIII)

ii) treating the compound of formula (VIII) with a compound M selected from N,N'-diisobutylethylenediamine, N,N'-dicyclohexylethylenediamine, and N,N'-dicyclopentylethylenediamine to produce the compound of formula (II).

5. The process according to claim 4, wherein the base used in step i) is selected from sodium hydroxide, sodium acetate, potassium hydroxide, ammonium hydroxide, sodium carbonate, potassium carbonate, sodium bicarbonate, triethylamine, diethylamine, tributylamine, pyridine, N-methylanilines, N-methylmorpholine and mixtures thereof.

6. The process according to claim 4, wherein the solvent used in step i) is selected from ethanol, methanol, isopropanol, THF, cyclohexanol, acetonitrile, DMAc, DMF, N-methyl pyrrolidine, ethyl acetate, methylene dichloride, ethylene dichloride, acetone, toluene, tetrahydrofuran, xylene, water and mixtures thereof.

7. A process according to claim 4, further comprising converting the compound of formula (II) into a compound of formula (I) by dissolving the compound of formula (II) in a mixture of organic solvents followed by treating the clear solution with an acid or with a sodium exchanging reagent to produce the compound of formula (I)

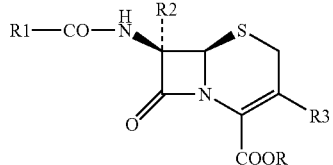

wherein $R^1$, $R^2$ and $R^3$ are the same as defined above and R is hydrogen or a pharmaceutically acceptable sodium salt.

8. The process of claim 7, wherein the sodium exchanging reagent is selected from sodium acetate, sodium citrate, sodium lactate, sodium ethylacetoacetate and sodium 2-ethylhexanoate and the solvent used for dissolving sodium exchange reagent is selected from ethanol, methanol, isopropanol, acetonitrile, ethyl acetate, acetone, water and mixtures thereof.

9. The process of claim 7, wherein the acid is selected from HCl, sulfuric acid, formic acid, acetic acid, perchloric acid, benzenesulfonic acid, p-toluenesulfonic acid, naphthalenesulfonic acid, methanesulfonic acid, trifluoro acetic acid, and mixtures thereof.

* * * * *